United States Patent
Brauns

(10) Patent No.: US 9,925,174 B2
(45) Date of Patent: Mar. 27, 2018

(54) ADMINISTRATION FORM FOR THE ORAL APPLICATION OF 3-[(2-{[4-(HEXYLOXYCARBONYL-AMINO-IMINO-METHYL)-PHENYLAMINO]-METHYL}-1-METHYL-1H-BENZIMIDAZOL ACID ETHYL ESTER AND THE SALTS THEREOF

(75) Inventor: Ulrich Brauns, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 100 days.

(21) Appl. No.: 11/381,890

(22) Filed: May 5, 2006

(65) Prior Publication Data

US 2006/0183779 A1 Aug. 17, 2006

Related U.S. Application Data

(63) Continuation of application No. 10/383,198, filed on Mar. 6, 2003, now abandoned.

(60) Provisional application No. 60/421,896, filed on Oct. 29, 2002, provisional application No. 60/409,762, filed on Sep. 11, 2002.

(30) Foreign Application Priority Data

Mar. 7, 2002 (DE) .................................. 10209985
Sep. 30, 2002 (DE) .................................. 10245624

(51) Int. Cl.
C07D 401/12 (2006.01)
A61K 31/4439 (2006.01)

(52) U.S. Cl.
CPC ........ *A61K 31/4439* (2013.01); *C07D 401/12* (2013.01)

(58) Field of Classification Search
USPC ............... 514/388, 338, 576, 574; 546/273.7
See application file for complete search history.

(56) References Cited

U.S. PATENT DOCUMENTS

| | | | |
|---|---|---|---|
| 3,887,705 A | 6/1975 | Serre et al. | |
| 3,968,111 A | 7/1976 | Bach et al. | |
| 4,003,909 A | 1/1977 | Narayanan et al. | |
| 4,361,546 A | 11/1982 | Stricker et al. | |
| 4,367,217 A * | 1/1983 | Gruber et al. ................ | 424/494 |
| 4,427,648 A * | 1/1984 | Brickl et al. .................. | 424/459 |
| 4,438,091 A * | 3/1984 | Gruber et al. ................ | 424/465 |
| 4,572,833 A | 2/1986 | Pedersen et al. | |
| 4,596,705 A | 6/1986 | Schepky et al. | |
| 4,675,405 A | 6/1987 | Musser et al. | |
| 4,728,660 A * | 3/1988 | Haynes et al. ................ | 514/356 |
| 4,786,505 A | 11/1988 | Lovgren | |
| 4,999,226 A | 3/1991 | Schock et al. | |
| 5,051,262 A | 9/1991 | Panoz et al. | |
| 5,286,736 A | 2/1994 | Soyka et al. | |
| 5,320,853 A * | 6/1994 | Noda et al. .................. | 424/472 |
| 5,387,593 A | 2/1995 | Mattson et al. | |
| 5,395,626 A | 3/1995 | Kotwal | |
| 5,416,099 A * | 5/1995 | Hartman et al. .............. | 514/323 |
| 5,434,150 A | 7/1995 | Austel et al. | |
| 5,478,828 A | 12/1995 | Mattson et al. | |
| 5,482,948 A | 1/1996 | Soyka et al. | |
| 5,637,320 A | 6/1997 | Bourke et al. | |
| 5,670,172 A * | 9/1997 | Buxton et al. ................ | 424/495 |
| 5,705,190 A | 1/1998 | Broad et al. | |
| 5,783,215 A | 7/1998 | Arwidsson et al. | |
| 5,800,836 A | 9/1998 | Morella et al. | |
| 5,912,014 A * | 6/1999 | Stern et al. .................. | 424/474 |
| 5,914,132 A * | 6/1999 | Kelm et al. .................. | 424/478 |
| 6,015,577 A * | 1/2000 | Eisert et al. ................. | 424/451 |
| 6,039,975 A * | 3/2000 | Shah et al. .................. | 424/473 |
| 6,086,918 A * | 7/2000 | Stern et al. .................. | 424/474 |
| 6,087,380 A * | 7/2000 | Hauel et al. ................. | 514/336 |
| 6,120,802 A * | 9/2000 | Breitenbach et al. ........ | 424/464 |
| 6,165,507 A | 12/2000 | Chariot et al. | |
| 6,248,770 B1 * | 6/2001 | Ries et al. .................... | 514/394 |
| 6,309,666 B1 * | 10/2001 | Hatano et al. ............... | 424/463 |
| 6,387,917 B1 | 5/2002 | Illum et al. | |
| 6,414,008 B1 * | 7/2002 | Hauel et al. ................. | 514/394 |
| 6,469,039 B1 * | 10/2002 | Hauel et al. ................. | 514/394 |
| 6,620,439 B1 * | 9/2003 | Mehta ........................... | 424/497 |
| 6,710,055 B2 | 3/2004 | Hauel et al. | |
| 6,900,229 B2 | 5/2005 | Hauel et al. | |
| 7,070,805 B2 | 7/2006 | Shimizu et al. | |
| 7,189,743 B2 | 3/2007 | Hauel et al. | |
| 7,202,368 B2 | 4/2007 | Zerban et al. | |
| 7,271,272 B2 | 9/2007 | Hwang et al. | |
| 7,316,819 B2 * | 1/2008 | Crotts et al. ................. | 424/464 |
| 7,932,273 B2 | 4/2011 | Schmid et al. | |
| 8,399,678 B2 * | 3/2013 | Gnad et al. ................. | 546/273.4 |

(Continued)

FOREIGN PATENT DOCUMENTS

CA 2256751 A1 2/1998
CA 2435492 A1 8/2002
(Continued)

OTHER PUBLICATIONS

Bastin, Richard J. et al. (Organic Process Research and Development 2000, 4, No. 5, 427-435).*
Exparte Norbert Hauel, Appeal 2011-010664, U.S. Appl. No. 10/383,198, Technology Center 1600.*
Paradaxa (dabigatran etexilate), Dabigatran etexilate mesilate is Ethyl N-{[2-({[4-((E)-amino{[hexyloxy)carbonyl]imino}methyl)phenyl]amino}methyl )-1-methyl-1 H-benzimidazol-5-yl]carbonyl}-N-pyrid in-2-yl-13-alan inate methanesulfonate, Jun. 11, 2013.*
Hauel, N. H., "Structure-Based Design of Novel Potent Nonpeptide Thrombin Inhibitors", J. Med. Chem. 2002, 45, 1757-1766, XP-001098844.
Caira, M. R.: "Crystalline Polymorphism of Organic Compounds", Topics in Current Chemistry, Bd.198, XP 001156954, pp. 163-208, 1998.

(Continued)

*Primary Examiner* — Sabiha N Qazi
(74) *Attorney, Agent, or Firm* — Marc Began; Philip I. Datlow

(57) ABSTRACT

The invention relates to a new administration form for the oral application of the active substance ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate and the pharmacologically acceptable salts thereof.

20 Claims, 1 Drawing Sheet

(56) References Cited

U.S. PATENT DOCUMENTS

| | | | |
|---|---|---|---|
| 2001/0010825 A1 | 8/2001 | Shimizu et al. | |
| 2003/0004181 A1 | 1/2003 | Hauel et al. | |
| 2003/0017203 A1* | 1/2003 | Crotts et al. | 424/477 |
| 2003/0181488 A1 | 9/2003 | Brauns | |
| 2004/0258749 A1 | 12/2004 | Guldner et al. | |
| 2005/0038077 A1 | 2/2005 | Kohlrausch et al. | |
| 2005/0095293 A1 | 5/2005 | Brauns et al. | |
| 2005/0107438 A1 | 5/2005 | Radtke et al. | |
| 2005/0234104 A1 | 10/2005 | Schmid et al. | |
| 2006/0183779 A1 | 8/2006 | Brauns et al. | |
| 2006/0222640 A1 | 10/2006 | Reilly et al. | |
| 2006/0247278 A1 | 11/2006 | Sieger et al. | |
| 2006/0276513 A1 | 12/2006 | Hauel et al. | |
| 2007/0105753 A1 | 5/2007 | Eisert et al. | |
| 2007/0149589 A1 | 6/2007 | Zerban et al. | |
| 2007/0185173 A1 | 8/2007 | Zerban et al. | |
| 2007/0185333 A1 | 8/2007 | Zerban et al. | |
| 2008/0317848 A2 | 12/2008 | Gramatte et al. | |
| 2009/0042948 A1 | 2/2009 | Sieger et al. | |
| 2011/0275824 A1* | 11/2011 | Gnad et al. | 546/273.4 |
| 2013/0052262 A1* | 2/2013 | Brueck et al. | 424/452 |

FOREIGN PATENT DOCUMENTS

| | | |
|---|---|---|
| CN | 103304539 | 9/2013 |
| CN | 103304539 A | 9/2013 |
| DE | 41 29 603 A1 | 3/1993 |
| DE | 19752843 A1 | 7/1999 |
| DE | 102 45 624 A1 | 4/2004 |
| EP | 0032562 A1 | 7/1981 |
| EP | 0088191 A2 | 1/1983 |
| EP | 0108898 A1 | 5/1984 |
| EP | 0 540 051 A1 | 5/1993 |
| EP | 0 547 517 A1 | 6/1993 |
| EP | 0 623 596 A1 | 11/1994 |
| EP | 0 655 439 A2 | 5/1995 |
| EP | 0942718 A1 | 9/1999 |
| EP | 1698623 | 6/2006 |
| EP | 1698623 A1 | 9/2006 |
| EP | 1870100 A1 | 12/2007 |
| JP | 58134033 | 8/1983 |
| JP | 03112928 U | 9/1989 |
| WO | WO 94/03160 | 2/1994 |
| WO | 9805320 A1 | 2/1998 |
| WO | 9825601 A1 | 6/1998 |
| WO | WO 98/37075 | 8/1998 |
| WO | 9856787 A1 | 12/1998 |
| WO | 00013671 A1 | 3/2000 |
| WO | 2000071118 A1 | 11/2000 |
| WO | 0234711 A1 | 5/2002 |
| WO | WO 03/007984 | 1/2003 |
| WO | 2003/030869 A1 | 4/2003 |
| WO | 2004/092129 A1 | 10/2004 |
| WO | 2005090382 A1 | 9/2005 |
| WO | 2006070878 A1 | 7/2006 |
| WO | 2011110876 | 2/2011 |
| WO | 2013110567 A1 | 8/2013 |

OTHER PUBLICATIONS

Nagahara, T. et al, "Dibasic (Amidlnoaryl) propancic Acid Derivatives as Novel Blood Coagulation Factyor Xa Inhibitors", J. Med. Chem. 1994, 37, pp. 1200-1207.

Berkowitz, Scott D., Anthrombotic Therapy after Prosthetic Cardiac Valve Implantation: Potential Novel Antithrombotic Therapies, American Heart Journal, vol. 142, No. 1 pp. 7-13 Results of Expert Meetings, XP-001146897, 2001.

Mungall, Dennis, , BIBR-1048 Boehringer Ingalheim, Current Opinion in Investigational Drugs, 2002 3(6) 905-907-XP-001147306.

Stangier, et al: Abstract of J thrombosis and Haemotosis, vol. 1, Supplement 1, Jul. 12-18, 2003.

Gustafsson, D., Abstract of J. Intern. Med Oct. 2003, 254 (4): 322-34; PMID: 12974871.

Stangier, et al; Abstract of The J. of Clinical Pharmacology, 2005; 45: 555-583.

The Merck Index 14th Edition, Merck & Co., NJ, USA, 2001, No. 9156, 4308, and 845, Ecuador, (Dec. 2006).

Berge, Stephen, M; Pharmaceutical Salts; Journal of Pharmaceutical Sciences; Review Article (1977) vol. 66, No. 1 pp. 1-19.

Non-Final Office Action dated Jun. 29, 2007 from U.S. Appl. No. 10/934,140, filed Sep. 3, 2004.

Response dated Dec. 31, 2007 from Non-Final Office Action dated Jun. 29, 2007; U.S. Appl. No. 10/934,140, filed Sep. 3, 2004.

Non-Final Office Action dated Apr. 4, 2008 from U.S. Appl. No. 10/934,140, filed Sep. 3, 2004.

Response dated Jul. 2, 2008 from Non-Final Office Action dated Apr. 4, 2008; U.S. Appl. No. 10/934,140, filed Sep. 3, 2004.

Final Office Action dated Dec. 2, 2008 from U.S. Appl. No. 10/934,140, filed Sep. 3, 2004.

Response dated Mar. 2, 2009 from Non-Final Office Action dated Dec. 2, 2008; U.S. Appl. No. 10/934,140, filed Sep. 3, 2004.

Non-Final Office Action dated Jun. 26, 2009 from U.S. Appl. No. 10/934,140, filed Sep. 3, 2004.

Response dated Nov. 27, 2009 from Non-Final Office Action dated Jun. 26, 2009; U.S. Appl. No. 10/934,140, filed Sep. 3, 2004.

Final Office Action dated Mar. 25, 2010 from U.S. Appl. No. 10/934,140, filed Sep. 3, 2004.

Stassen, "Ex Vivo Anticoagulant Activity of BIBR953ZW, A Novel Synthetic Direct Thrombin Inhibior and of its Prodrug BIBR1048 MS in Different Animal Species," Supplement to the Journal Thrombosis and Haemostasis, (2001).

Thoma, Aus Dern Institut fur Pharmazie, "Retardation of Weak Basic Drugs", 1989.

Thoma, Aus Dern Institut fur Pharmazie, "Retardation of Weak basic Drugs, 2nd Comm., Optimization of availability with Papaverine and Codeine in diffusion pellets", 1989.

Thoma, Aus Dern Institut fur Pharmazie, "Retardation of Weak basic Drugs, 5th Comm., Optimization of availability with Papaverine and Codeine in diffusion pellets", 1989.

Stangier et al., "Pharmacokinetics of BRBR953 ZW, A Novel Low Molecular Weight Direct Thrombin Inhibitor in Healthy Volunteers," Supplement to the Journal Thrombosis and Haemostasis (2001).

Wienen, Supplement to the Journal Thrombosis and Haemostasis, "Effects of the Direct Thrombin Inhibitor BIBR 9532W and its orally active pro-drug BIBR1048MS on experimentally induced clot formation and template bleeding time in rats", 2001.

Swarbrick, Encyclopedia of Pharmaceutical Terminology, Third Edition, 2011.

Gould, International Journal of Pharmceutics, "Salt Selection for basic drugs", 1986.

Streubel, Journal of Controlled Release, "pH and independent release of a weakly based drug from water-insoluble and soluble matrix tablets", 2000.

Venkatesh, Pharmacetical Development and Technology, "Development of controlled release SK&F 82526-J Buffer Bead Formulations with a Tartaric Acid as the Buffer", 1998.

Busch, Supplement to the Journal Thrombosis and Haemostasis, "Pharmacokinetics of the Synthetic Direct Thrombin Inhibitor BIBR953 ZW in Different Animal Species", 2001.

Shargel, Applied Biopharmaceutics and Pharmacokinetics, 4th Edition, "Physiologic Factors related to Drug Absorption", 1999.

Shargel, Applied Biopharmaceuticals and Pharmacokinetics, "Biopharmaceutic Considerations in Drug Product Design", 1999.

Rudnic, Remington: The Science and Practice of Pharmacy, "A treatise in the theory and practice of pharmaceutical sciences", 2000.

Gabr, European Journal Pharmacy, "Effect of Organic Acids on the Release Patterns of Weakly Basic Drugs from Inert Sustained release Matrix Tablets", 1992.

Racynska, Journal Chem. Society, "Hydrogen Bonding Basicity of Amidines", 1988.

Streng, Journal of Pharmaceutical Sciences, "General treatment of pH-Solubility Profiles of Weak Acids and Bases and the effects of Different Acids on the Solubility of a weak base", 1984.

(56) References Cited

OTHER PUBLICATIONS

Elder, Wiley Interscience, "The Utility of Sulfonate Salts in Drug Development", 2010.
Stahl, Handbook of Pharmaceutical Salts, 2002.
Engel, International Journal of Pharmaceutics, "Salt Form Selection and Characterization of LY 333531 Mesylate Monohydrate", 2000.
Wienen, Supplement to the Journal of Thrombosis and Haemostasis, "Antithrombotic effects of the Direct Thrombin Inhibitor BIBR9532ZW and its orally active Pro-drug BIBR1048MS in a model of venous thrombosis in rabbits", 2001.
Calcium Nitrate Database, 2014.
Bendelin, Pharmaceutical Dosage Forms, vol. 1, Second Edition, Revised and expanded, p. 1-60, 1989.
Stassen, Supplement to the Journal of Thrombosis and Haemostasis, "Pharmacodynamics of the Synthetic Direct Thrombin Inhibitor BIBR9523ZW in Healthy Subjects", 2001.
Porter, Remington: The Science and Practice of Pharmacy, 20th Edition, 2000.
Second Declaration of Dr. Sieger, for U.S. Appl. No. 10/383,198, filed Jan. 13, 2014.
Third Declaration for Dr. Sieger, for U.S. Appl. No. 10/383,198, filed Jan. 13, 2014.
Swarbrick, Encyclopedia of Medical terminology, 2011.
Patent Grant in Opposition CN 03805473 dated May 8, 2009.
SIPO Request Acceptance in Opposition CN 03805473 dated Nov. 27, 2012.
Final Post Hearing Statement in Opposition in CN 03805473 dated Mar. 8, 2013.
SIPO decision in Opposition CN 03805473 dated Apr. 27, 2013.
Final Complaint in Opposition in CN 03805473 dated Aug. 14, 2013.
Administrative Answer Brief in Opposition CN 03805473 dated Feb. 24, 2014.
Post Hearing Statement Plaintiff in Opposition CN 03805473 dated Mar. 12, 2014.
Administrative Judgment Hearing-Beijing, in Opposition CN 0380574 dated Mar. 20, 2014.
Opposition Papers for IL 163863 dated Sep. 30, 2013.
Opposition Papers for IL 638863 (2) dated Sep. 30, 2013.
Opposition Papers for IL 209638 dated Feb, 26, 2013.
Opposition Papers for IL 209638 dated May 25, 2015.
International Search Report for PCT/EP03/02141 dated Apr. 29, 2003.
Remington Pharmacia, Gennero R. Alfonso, 19th Edition, Panamericana, 1988, p. 2470.
Rote Liste Fachinformationen: "Drug Information on Pradaxa" http://www.fachinfo.de/data/fi/jsearch?wirkstoff; Jan. 2002.
EMEA, Committee for Veterinary Medicinal products, "Tricaine Mesilate", 1999.
WHO Drug Information, International Proprietary Names for Pharmaceutical Substances, 2000.
Submission of Patentee, EP09725292, 2011.
Creasey, Chemical Defence Experimental Establishment, "2-Hydroxyiminomethyl-N-Methylpyridinium Methanesulphonate (P2S), an antidote to Organphosphrous Poisoning, its preparation, estimation and stability", 1959.
Technical Data, filed by the patentee in the examination procedure as annex wiht the written submission og Mar. 28, 2011, EP07115663, "Solubility of BIBR 1048 Salts in Water", 2011.
WHO Drug Infomation, International Proprietary names for Pharmaceutical Substances, vol. 16, No. 2, 2002.
Full Prescribing Information for Pradaxa, 2011.
Russell, et al., Pharmaceutical Research, "pH-related changes in the Absorption of Dipyridamole in the Elderly", 1994, vol. 11, No. 1, p. 136-143.
IUPAC-Gold Book, Definition of Solubility, 2013.
IUPAC-Gold Book, definition of saturated solution, 2013.
Experimental Report, Crystallinity and Stability Tests of Dabigatran Etexilate Salts, 2012, p. 1-3.
Pradaxa 2013, p. 1-37.
Anvisa, National Health Surveillance Agenxy, technical note No. 003/2013/CEFAR/CEFAR/GGHED/ANVISA p. 1-5.
Certificate District Court Mainz (2010).
Guthier, Can. J. Chem, "Hydrolysis of esters of oxy acids:pK values for strong acids; Bronsted relationship for attack of water at methyl; free energies of hydrolysis of esters of oxy acids; and a linear relationship between free energy of hydrolysis and pKa holding over a range of 20pK units", 56, 1978, p. 2342-2354.
Translation of Interlocutory Decision of Opposition of EP 1489054 dated Jul. 3, 2014. (1).
Chemistry Review for NDA 22-512, Pradaxa Capsules, US Food and Drug Administration (FDA) (2010).
Response to Second Office Action in Opposition CN03805473 dated Jul. 23, 2008.
Response to First Office Action in Opposition CN 03805473 dated May 25, 2006.
Opponent Submission of Opposition of EP 1489054 dated Jul. 22, 2014.
Translation of Interlocutory Decision of Opposition of EP 1489054 dated Jul. 3, 2014 (2).
Notice of Opposition in EP 1870100 dated Nov. 1, 2012.
Second Notice of Opposition in EP 1870100, dated Oct. 2, 2012.
Patentee Reply in Opposition in EP 1870100, dated Jun. 7, 2013.
NPL data in Opposition in EP 1870100 dated Dec. 20, 2013.
Patentee Written Submission in Opposition in EP 1870100 dated Jan. 10, 2014.
Patentee Written Submission in opposition in EP 1870100 dated Jan. 13, 2014.
Opponent Written Submission for Opposition in EP 1870100 dated Jan. 24, 20134.
Opponent Written Submission in Opposition in EP 1870100 dated Jan. 28, 2014.
Patentee Written Submission in Opposition EP 1870100 dated Mar. 20, 2014.
Opposition Results for EP1870100 dated Mar. 28, 2014.
Patentee Reply in Oppostion in EP 1485094 dated Mar. 27, 2013.
Notice of Opposition for Opposition in EP 1485094 dated Mar. 27, 2013.
Second Notice of Opposition for Opposition in EP 1485094 dated Apr. 3, 2013.
Opposition Results for EP 1485094 dated Apr. 4, 2014.
Notice of Appeal in Opposition of EP 1485094 dated Jul. 2, 2014.
International Search Report for PCT/EP 0302141 dated Apr. 29, 2003.
WHO Drug Information, INN List 46, 2001, vol. 15, No. 3 and 4.
EMEA, CHMP Assessment Report for Pradaxa 2008, pp. 6 and 7.
International Search Report for PCT/EP0302184 dated Aug. 12, 2003.
Allinger, excerpt from Organic Chemistry, 1980, p. Title Page plus p. 816-817.
Roempp, excerpt from Pharmaceutical Dictionary, 1986, p. title page plus p. 152-155; 3694-3697.
Burger, excerpt from Pharmaceutical Dictionary, 8th Edition, 1998, p. title page plus p. 497-498.
Foroughifar, Can. J. Chem, "Basicity of substituted 2-pyridyl-1,1,3,3-tetramethylguanidines and aminopyrimidines in acetonitrile and water solvents", downloaded from www.nrcresearchpress.com, retrieved online from Ingelheim Hosting site on Nov. 20, 2013, 1992.
Prosecution Papers for JP3866715 dated Apr. 28, 2006.
Prosecution Papers for JP3866715 dated Mar. 5, 2010.
Prosecution Papers for JP386615 dated 2008.
Luche, excerpt from Synthetic Organic Chemistry,1998, p. title page plus p. XX.
Shargel, Applied Biopharmaceutics and Pharmacokinetics, "Biopharmacetic Considerations in Drug Product in Drug Product in Drug Product Design" 4th Edition, p. 13-14, 1999.
Solvias, Experimental Report, "Dabigatran Extexilate Salt formation and Solubility Measurements" p. 1-55, 2014.
Reiser, Declaration of Technical Expert, "Dabigatran etexilate and its salts to be formulated in a special pharmaceutical composition" p. 1-12, 2014.

(56) References Cited

OTHER PUBLICATIONS

Badawy, International Journal of Pharmaceuticals, 223, "Effect of salt form on chemical stability of an ester prodrug of a glycoprotein b/IIIa receptor antagonist in solid dosage forms" p. 81-87, 2001.
Solvias AG, HPLZ analytics by Solvias of tartrate salt sample SP220-LTA-P1, dated Jul. 24, 2014.
European Medicines Agency, CHMP assessment report for Pradaxa, dabigatran etexilate, 2008. p. 1-36.
Badawy, International Journal of Pharmaceutics, 223, "Effect of Salt form on chemical stability of an ester prodrug of a glycoprotein b/IIIa receptor antagonist in solid dosage forms", p. 81-87, 2001.
China Pharmacist, 2008, vol. 11, p. 523-529.
Dalton and Yates, Encyclopedia of Pharmaceutical Technology, "Bioavailability of drugs an Bioequivalence in Swarbrick", 3rd Edition, 2007, p. 1012-1022.
European Medicines Agency, CHMP assessment report for Pradaxa, 2008, p. 1-36.
European Pharmacopoeia, 4th Edition, 2002, p. 1.
Excerpt from CHMP Assessment report for Pradaxa, 2015, p. 7, p. 16.
Experimental Report, Stability of the claimed Dabigatran etexilate formulation, p. 1-4, 2014.
Harmsen, et al., Mol. Immunol. 2000 Aug. 2007 (10) 579-90.
International Journal of Pharmaceutical research, 1978, No. 3, p. 145-152.
Janeway, Immunology, 3rd Ed., 1997, Garland Press, pp. 3:1-3:11.
Koskimies, et al., Int. J. Clin. Pharmacol. Ther. vol. 51, No. 10, 2013, "Oral Bioavailability of ospemifene improves with food intake", p. 787-794.
Notice of Opposition, dated Apr. 3, 2013.
Patent Proprietor's Submissions in opposition proceedings relating to EU patent 1870100, Jun. 7, 2013.
Paul, Fundamental Immunology, 3rd Ed., 1993, p. 242.
Pharmacopoeia of the People's republic of China, Industrial Press, vol. II, 2000, No. 3 Appendix XIXC: Guidelines for Chemical Drug Stability, cover page, copyright page, 6 pages, 2015.
Pharmacy, The People's Medical Publishing House, 1999, p. 13-29.
Pharmacy, The People's medical Publishing house, 5th Edition, 2004, p. 223.
Portolano, et al., Immonol., 1993, 150:880-887.
Progress in Pharmaceutical Science, 2012, vol. 36, p. 151-157.
Reiser, Declaration of Technical Expert, "Dabigatran etexilate and its Salts to be formulated in a special pharmaceutical composition", p. 1-12, 2014.
Rudikoff, et al, Proc Natl Acad Sci USA, 1982, 79:1979-1983.
Shargel, Applied Biopharmaceutics and Pharmacokinetics, "Biopharmaceutic Considerations in Drug Product Design", 4th Edition, p. 13-14, 1999.
Solubility data of dabigatran etexilate free base and different salts thereof, 2015.
Solvias AG, Experimental Report, "Dabigatran Extexilate Salt Formation and Solubility Measurements", p. 1-55, 2014.
Solvias AG, HPLZ analytics by Solvias of tartrrate salt sample SP-220-LTA-P1, Opposiiton papers, dated Oct. 4, 2011.
Stumpp, et al., Drug Discovery Today, 2008, 13(15-16):695-701 doi:10.1016/j.drudis.2008.04.013 EPUB 2008.
Third Party Observation for Application No. EP20070115663, "Ethyl 3-(2-(4-hexyloxycarbonylamidino) phenylaminomethyl)-1-methyl-1H-benzimidazole-5-carbonyl)-2-pyridylamino)propionate methansulfonate." 2016.
Trillo, Professor C. Fauli "Discussion of Galenic Pharmacy." Luzan 5, 1993, pp. 83-84.

Cater et al., "The Clinical Importance of Hypochlorhydria (A Consequence of Chronic Helicobacter Infection): Its Possible Etiological Role in Mineral and Amino Acid Malabsorption, Depression, and Other Syndromes", Medical Hypotheses, 1992, vol. 39, pp. 375-383.
Chin et al., "Effects of an Acidic Beverage (Coca-Cola) on Absorption of Ketoconazole", Antimicrobial Agents and Cfiemotiierapy, Aug. 1995, vol. 39, No. 8, pp. 1671-1675.
Clayden, et al., "Organic Chemistry." Oxford University Press, 2001, pp. 202 and 286.
Dotherty et al., "Microenvironmental pH control of drug dis solution", International Journal of Pharmaceutics, 1989, col. 50, pp. 223-232.
DrugBank: Aniline, Accession No. DB06728, 2010, pp. 1-7.
DrugBank: Benzamidine, Accession No. DB03127 (EXPT00669), 2005, pp. 1-10.
Eisert et al., "Dabigatran: An Oral Novel Potent Reversible Nonpeptide Inhibitor of Thrombin", Arterioscler Thromb Vasc Biol., Jul. 29, 2010, 30:1885-1889.
EMA, Summary of Product Characteristics for Pradaxa 75mg, Annex I, 2008, pp. 1-23.
Fauli et al., Tratado de Farmacia Galència, Luzàn 5, 1993, pp. 83-84.
Gomes-Outes et al., "Discovery of Anticoagulant Drugs: A Historical. Perpspective ", Current Drug Discovery Technologies, 2012, 83-104.
Harter et al., "Anticoagulation Drug Therapy: A review", Western Journal Emergy Medicine, Jan. 2015, vol. XVI No. 1.
Himmelsbach et al., "Design of Highly Potent Nonpeptidic Fibrinogen Receptor Antagonists", pp. 243-254.
Joule, J.A. et al., "Heterocycles containing more than two hetero atoms." Heterocyclic Chemistry, Fourth Edition, 2000, p. 513.
Keenan, Richard M. et al., "Conformational Preferences in a Benzodiazepine Series of Potent Nonpeptide Fibrinogen Receptor Antagonists." Journal of Medical Chemistry, 1999, vol. 42, pp. 545-559.
Knapp et al., "Modification of gastric pH with oral glutamic acid hydrochloride", Clinical Pharmacy, Research, vol. 10, Nov. 1991, pp. 866-869.
Kocienski, Philip J., "Protecting Groups." University of Leeds, 3rd Edition, 2005, p. 517.
Müller et al., "Profound and Sustained Inhibition of Platelet Aggregation by Fradafiban, a Nonpeptide Platelet Glycoprotein I Ib/IIIa Antagonist, and Its Orally Active Prodrug, Lefradafiban, in Men", Circulation Articles, 1997, vol. 96, pp. 1130-1138.
Repic, Oljan Ph.D., "Principles of Process Research and Chemical Development in the Pharmaceutical Industry." Sandoz Pharmaceuticals Corporation, 1988, pp. 10-13.
Slanger et al., "Management of gastric achlorhydria and Hypochlorhydria", Geriatrxcs, Aug. 1966, pp. 193-198.
Stangier, J. et al., "Pharmacology, Pharmacokinetics, and Pharmacodynamics of Dabigatran Etexilate, an Oral Direct Thrombin Inhibitor." Clinical and Applied Thrombosis/Hemostasis, 2009, vol. 15, No. 1S, pp. 9S-16S.
Thoma et al., "Retardation of weakly basic drugs with diffusion tablets", International Journal of Pharmaceutics, 1990, vol. 58, pp. 197-202.
Thoma et al., "The pH-independent release of fenoldopam from pellets with insoluble film coats1", European Journal of Pharmaceutics and Biopharmaceutics, 1998, vol. 46, pp. 105-113.
Wangs et al., "Effect of food and gastric acidity on absorption of orally administered ketoconazole", Clinical Pharmacy, Research Ketoconazole, 1988, vol. 7, pp. 228-235.
Weller at al., "Orally Active Fibrinogen Receptor Antagonists. 2. Amidoximes as Prodrugs of Amidines", Journal of Medicinal Chemistry, 1996, vol. 39, No. 16, pp. 3139-3147.
Gennaro, Alfonso, R.; Remington Farmacia 19th Edition, Panamericana Espana 1988, p. 2470, Ecuador (Dec. 2006).
Prosecution Papers for JP 3866715 dated Apr. 28, 2008.
Prosecution Papers for JP 3866715 dated 2008.
Prosecution Papers for JP 3866715 dated Mar. 5, 2010.

* cited by examiner

Schematic structure of the pharmaceutical composition:

Core material
Containing organic acid

Insulating layer

Active substance layer coating (optional)

ADMINISTRATION FORM FOR THE ORAL APPLICATION OF 3-[(2-{[4-(HEXYLOXYCARBONYL-AMINO-IMINO-METHYL)-PHENYLAMINO]-METHYL}-1-METHYL-1 H-BENZIMIDAZOL ACID ETHYL ESTER AND THE SALTS THEREOF

RELATED APPLICATION

This application is a continuation of pending U.S. application Ser. No. 10/383,198, which claims benefit of U.S. Provisional Application No. 60/421,896, filed on Oct. 29, 2002 and U.S. Provisional Application No. 60/409,762, filed on Sep. 11, 2002, the contents of which are herein incorporated by reference.

FIELD OF INVENTION

The invention relates to administration forms for oral applications of prodrugs and in particular prodrugs of the active substance ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate and the pharmacologically acceptable salts thereof.

BACKGROUND OF THE INVENTION

The invention relates to an administration form for the oral application of the active substance ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate and the pharmacologically acceptable salts thereof. This active substance having the chemical formula

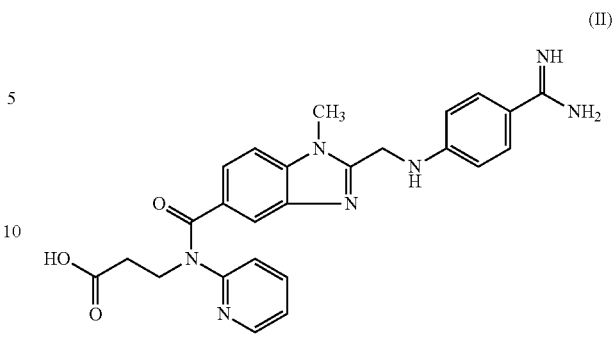

is already known from WO 98/37075, which discloses compounds with a thrombin-inhibiting effect and the effect of prolonging the thrombin time, under the name 1-methyl-2-[N-[4-(N-n-hexyloxycarbonylamidino)phenyl]-amino-methyl]-benzimidazole-5-yl-carboxylic acid-N-(2-pyridyl)-N-(2-ethoxycarbonylethyl)-amides. The compound of formula I is a double prodrug of the compound

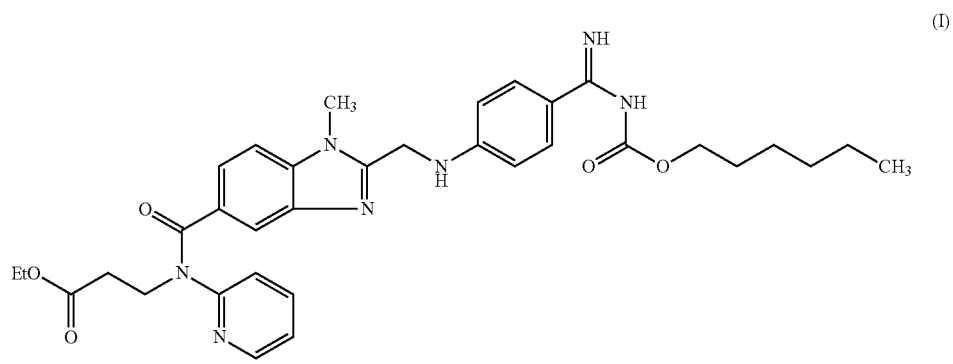 [SMILES: CCCCCCOC(=O)NC(=N)c1ccc(NCc2nc3cc(C(=O)N(CCC(=O)OCC)c4ccccn4)ccc3n2C)cc1]

i.e. the compound of formula I is only converted into the active compound, namely the compound of formula II, after entering the body. The main indication for the compound of chemical formula I is the post-operative prevention of deep-vein thrombosis.

DESCRIPTION OF THE INVENTION

The aim of the invention is to provide an improved formulation for oral use of the compound of formula I (which is also referred to hereinafter as the "active substance").

Surprisingly it has now been found that the use of pharmaceutically acceptable organic acids with a water solubility of >1 g/250 ml at 20° C., preferably >1 g/160 ml at 25° C., in solid oral preparations leads to a significantly improved formulation of ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate as well as the pharmaceutically acceptable salts thereof.

Pharmaceutically suitable acids for the purposes of this invention are for example tartaric acid, fumaric acid, succinic acid, citric acid, malic acid, glutamic acid and aspartic acid including the hydrates and acid salts thereof. Particularly suitable for the purposes of this invention are tartaric acid, fumaric acid, succinic acid and citric acid.

Figure 1:
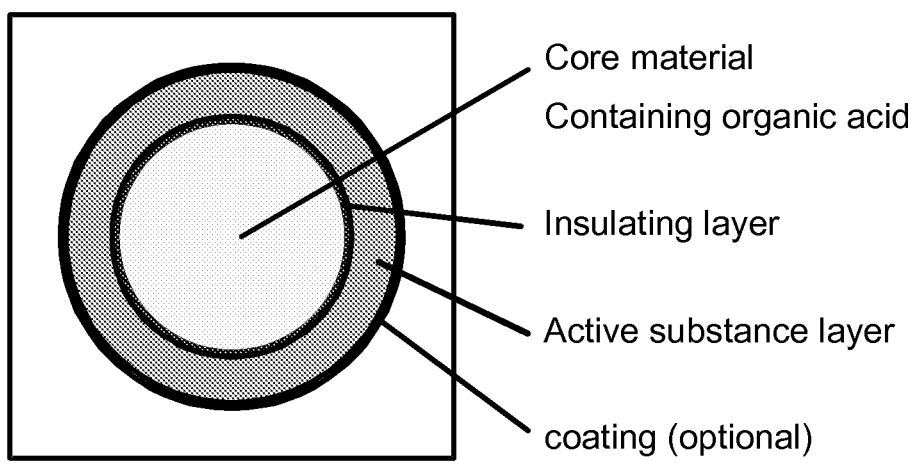
FIG. 1 shows a schematic structure of the pharmaceutical composition.

A preferred embodiment of the invention is a multiparticulate preparation in which the individual particles are constructed as in FIG. 1.

FIG. 1 shows the diagrammatic structure of the pharmaceutical composition by means of a section through a pellet suitable for the preparation of the pharmaceutical composition according to the invention. The roughly bead-shaped/spherical core region of this pellet contains/consists of the pharmaceutically acceptable organic acid. Then follows a layer, the so-called insulating layer, which separates the acid core from the layer containing the active substance. The insulating layer is in turn surrounded by the equally spherically shaped layer of active substance which may in turn be enclosed in a coating which increases the abrasion resistance and shelf life of the pellets.

One advantage of the formulation thus constructed is the spatial separation of the organic acid and active substance by the insulating layer. A further advantage of the construction of the pellets as described above is the fact that the organic acid does not go into solution until after the preparation has been taken and then produces an acid microclimate in which the active substance can dissolve.

The core material used is a pharmaceutically acceptable organic acid with a water solubility of >1 g/250 ml at 20° C., such as e.g. tartaric acid, fumaric acid, succinic acid, citric acid, malic acid, glutamic acid and aspartic acid including the hydrates and acid salts thereof, to which a small amount of 1 to 10% by weight, preferably 3 to 6% by weight of a suitable binder is optionally added. The use of a binder may be necessary, for example, if the starting acids are produced by a pan build-up process. If the method used is extrusion or spheronisation, other technological adjuvants such as microcrystalline cellulose will be needed instead of binders. It is also possible to use pure (100%) acid as the starting material if it can be obtained in a sufficiently narrow range of particle sizes. The pharmaceutically acceptable organic acids used are preferably tartaric acid, fumaric acid, succinic acid or citric acid; tartaric acid is particularly preferred. As binder, it is possible to use gum arabic or a partially or totally synthetic polymer selected from among the hydroxypropylcelluloses, hydroxypropylmethylcelluloses, methylcelluloses, hydroxyethylcelluloses, carboxymethylcelluloses, polyvinyl-pyrrolidone, the copolymers of N-vinylpyrrolidone and vinyl acetate, or combinations of these polymers; gum arabic is preferred. The spherical core material preferably has an average diameter of 0.4-1.5 mm. The content of the pharmaceutically acceptable organic acid is usually between 30 and 100% in the core material, corresponding to an amount of between 20 and 90%, preferably between 20 and 80% in the finished pellet (i.e. in the pharmaceutical composition).

To increase the durability of the finished product it is advantageous to coat the core material before the application of the active substance with an insulating layer based on a water-soluble, pharmaceutically acceptable polymer. Examples of such water-soluble polymers include for example gum arabic or a partially or totally synthetic polymer selected from among the hydroxypropylcelluloses, hydroxypropylmethylcelluloses, methylcelluloses, hydroxyethylcelluloses, carboxymethylcelluloses, polyvinylpyrrolidone, the copolymers of N-vinylpyrrolidone and vinyl acetate, or combinations of these polymers. Gum arabic or a hydroxypropylmethylcellulose is preferably used. If desired, the coating with the water-soluble, pharmaceutically acceptable polymer may be carried out with the addition of suitable plasticisers, separating agents and pigments, such as for example triethylcitrate, tributylcitrate, triacetin, polyethyleneglycols (plasticisers), talc, silicic acid (separating agents), titanium dioxide or iron oxide pigments (pigments).

The active substance layer contains the active substance ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate (BIBR 1048) or one of the pharmaceutically acceptable salts thereof as well as binders and optionally separating agents. A preferred salt of the active substance is the mesylate (methanesulphonate) of the compound of formula I. Suitable binders include for example hydroxypropylcellulose, hydroxypropylmethylcellulose, methylcellulose, hydroxyethylcellulose, carboxymethylcellulose, polyvinylpyrrolidone, copolymers of N-vinylpyrrolidone and vinyl acetate or combinations of these polymers. Preferably, hydroxypropylcellulose or copolymers of N-vinylpyrrolidone and vinyl acetate are used. The addition of separating agents such as e.g. talc or silicic acid serves to prevent the particles from aggregating during the process. The active substance content is 5 to 60%, preferably 10 to 50% of the pharmaceutical composition.

The optional outermost layer, which serves to reduce any increased abrasion during packing into capsules and/or to increase the shelf life, consists of pharmaceutically conventional film-forming agents, plasticisers and optionally pigments. Suitable film-forming agents include for example hydroxypropyl-cellulose, hydroxypropylmethylcellulose, methylcellulose, polymers and copolymers of acrylic and methacrylic acid and the esters thereof, or combinations of these polymers. Suitable plasticisers include inter alia triethylcitrate, tributylcitrate, triacetin or polyethyleneglycols. The pigments used may be e.g. titanium dioxide or iron oxide pigments. Preferably, the outer coating consists of hydroxypropylmethylcellulose and/or methylcellulose, optionally with the addition of polyethyleneglycols as plasticisers.

The pellets may be prepared by the method described hereinafter:

The acid-containing core material consists either of crystals of the particular organic acid used or, more advantageously, of roughly spherical particles of the desired size containing a large amount of organic acid, which can be produced by methods known and established in pharmaceutical technology. The core material may be produced, in particular, by pan methods, on pelleting plates or by extrusion/spheronisation. Then the core material thus obtained may be divided into fractions of the desired diameter by screening. Suitable core material has an average diameter of 0.4 to 1.5 mm, preferably 0.6 to 0.8 mm.

First, the insulating layer is applied to this acid-containing core material. This can be done by conventional methods, e.g. by applying an aqueous dispersion of the water-soluble, pharmaceutically acceptable polymer, optionally with the addition of plasticisers, separating agents and/or pigments, in a fluidised bed, in coating pans or in conventional film coating apparatus. If necessary the product can then be screened again.

Then the active substance is applied from a dispersion containing binder and optionally separating agent. The volatile dispersant is removed during or after the process by drying. Suitable binders in the dispersion may be for example hydroxypropylcellulose, hydroxypropylmethylcellulose, methylcellulose, hydroxyethylcellulose, carboxymethylcellulose, polyvinylpyrrolidone, copolymers of N-vinylpyrrolidone and vinyl acetate or combinations of these polymers. Preferably, hydroxypropylcellulose or copolymers of N-vinylpyrrolidone and vinyl acetate are used. Suitable separating agents include e.g. talc or silicic acid; preferably, talc is used. The dispersants may be for example ethanol, 2-propanol, acetone or mixtures of these solvents with one another or with water, preferably 2-propanol. The application of active substance to the core material may be carried out by established methods known in pharmaceutical technology, e.g. in coating pans, conventional film coating apparatus or by the fluidised bed method. Then a further screening process may be carried out.

To reduce any increased abrasion during transfer into capsules or to increase the shelf life the system may finally be coated with a coating of a pharmaceutically conventional film forming agent, plasticiser and optionally pigment. This may be done by conventional methods as mentioned earlier in the description of the application of the insulating layer.

When core material with an average diameter of 0.4-1.5 mm is used, the process described above produces pellets containing active substance, which can then be packed into hard capsules, for example. To do this, a number of these units corresponding to the required dosage are packed into hard capsules in a standard capsule filling machine. Suitable hard capsules include, for example, hard gelatine capsules or hard capsules of hydroxypropylmethylcellulose (HPMC); HPMC capsules are preferred. The active substance content of the pharmaceutical composition is 5 to 60%, preferably 10 to 50%; the content of the pharmaceutically acceptable organic acid is usually between 20 and 90%, preferably between 20 and 80%.

Unless otherwise stated, percentages specified are always percent by weight. All the data on the active substance content relate to the active substance base of formula I (not to a specific salt) unless otherwise stated.

Clinical Trials

In preliminary tests on test subjects with conventional tablets containing the compound of formula I it had been established that highly variable plasma levels occurred, with individual cases of malabsorption. The variability of the plasma level patterns is significantly lower after the administration of the compound of formula I as an orally administered solution; there were no cases of malabsorption under these circumstances.

Tests have shown that the compound of formula I dissolves relatively well in water at low pH levels, whereas at pH levels above 5 in accordance with the definition of the European Pharmacopoeia it is virtually insoluble. Therefore the volunteers in one branch of the clinical trials were given pantoprazole, which serves to produce an elevated gastric pH.

For example, the pharmaceutical compositions according to Examples 1 and 2 were tested for their bioavailability by comparison with a conventional tablet. To do this, the formulation prepared according to Example 1 containing 50 mg of active substance base per capsule was clinically tested for its bioavailability on a total of 15 volunteers. In one branch of the treatment, the volunteers were given the composition by mouth (=orally) on an empty stomach without any pre-treatment. In another branch of the treatment the same volunteers were pre-treated, prior to the oral administration of the composition, with 40 mg of pantoprazole b.i.d. (=twice a day) for three days by mouth to increase the gastric pH; the treatment with pantoprazole was continued during the administration of the formulation according to the invention.

The degree of absorption was determined by measuring the quantity of active metabolite of formula II excreted in the urine.

The relative bioavailability after pre-treatment with pantoprazole was 94% on average compared with administration without any pre-treatment.

Under comparable conditions of administration, the relative bioavailability (based on the area under the plasma concentration/time curve) of a tablet containing 50 mg of active substance, developed and produced according to the prior art and containing no water-soluble organic acid, after corresponding pre-treatment with pantoprazole, is 18%. Table I shows the precise composition of the tablet used:

TABLE I

| | Ingredient | mg/tablet |
| --- | --- | --- |
| Core | mesylate of the compound of form. I | 57.7 |
| | lactose monohydrate | 58.0 |
| | microcrystalline cellulose | 48.3 |
| | crospovidone | 3.4 |
| | magnesium stearate | 2.6 |
| Film coating | polyethyleneglycol 6000 | 0.56 |
| | titanium dioxide | 0.80 |
| | talc | 0.64 |
| | hydroxypropylmethylcellulose | 1.92 |
| | iron oxide yellow | 0.08 |
| | Total | 174.0 |

The relative bioavailability was thus improved by about a factor of 5 by using the formulation according to the invention.

The formulation prepared according to Example 2 containing 50 mg of active substance base per capsule was also clinically tested for its bioavailability on a total of 15 volunteers. In one branch of the treatment, the volunteers were given the composition by mouth on an empty stomach without any pre-treatment. In another branch of the treatment the same volunteers were pre-treated, prior to the oral administration of the composition, with 40 mg of pantoprazole b.i.d. for three days by mouth to increase the gastric pH; the treatment with pantoprazole was continued during the administration of the formulation according to the invention.

The degree of absorption was determined by measuring the quantity of the active metabolite of formula II excreted in the urine.

The relative bioavailability after pre-treatment with pantoprazole was 76% on average compared with administration without any pre-treatment.

Under comparable conditions of administration, the relative bioavailability (based on the area under the plasma concentration/time curve) of a tablet containing 50 mg of active substance, developed and produced according to the prior art and containing no water-soluble organic acid, after corresponding pre-treatment with pantoprazole, is 18%. Table II shows the precise composition of the tablet used:

TABLE II

| | Ingredient | mg/tablet |
| --- | --- | --- |
| Core | mesylate of the compound of form. I | 57.7 |
| | lactose monohydrate | 58.0 |
| | microcrystalline cellulose | 48.3 |

TABLE II-continued

| | Ingredient | mg/tablet |
|---|---|---|
| | crospovidone | 3.4 |
| | magnesium stearate | 2.6 |
| Film coating | polyethyleneglycol 6000 | 0.56 |
| | titanium dioxide | 0.80 |
| | talc | 0.64 |
| | hydroxypropylmethylcellulose | 1.92 |
| | iron oxide yellow | 0.08 |
| | Total | 174.0 |

Figure 2:
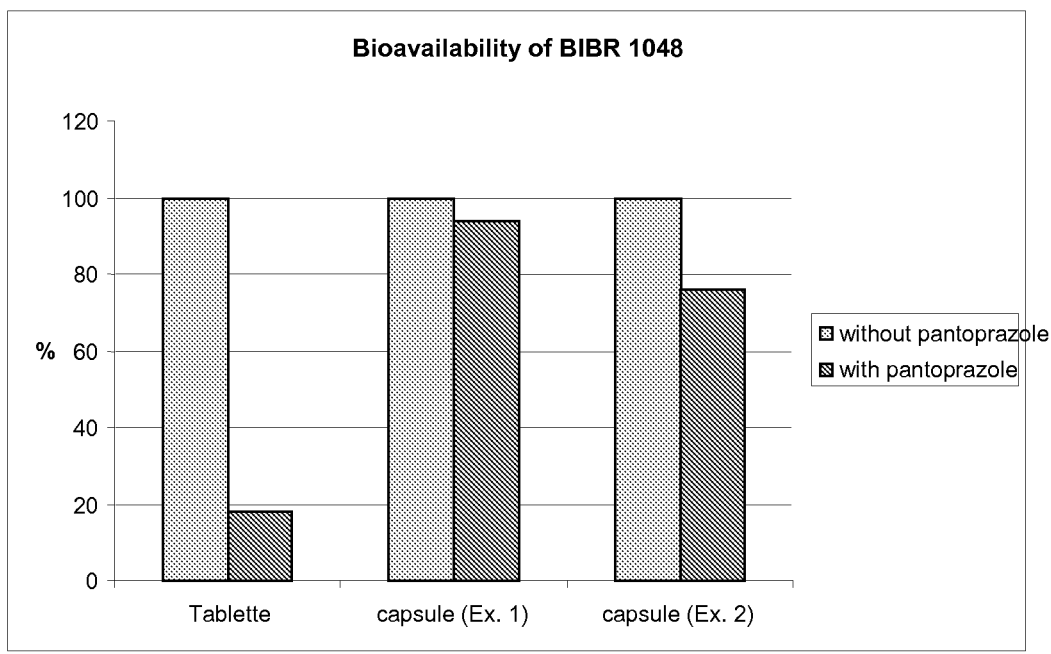
FIG. 2 shows the bioavailability of BIBR 1048.

The relative bioavailability of the active substance compared with conventional formulations was thus improved by about a factor of 4 by using the formulation according to the invention. The bioavailability of the two formulations according to the invention compared with the tablet described above with and without the simultaneous administration of pantoprazole is graphically illustrated in FIG. 2.

The clinical trials show another advantage of the preparation according to the invention containing the compound of formula I, which is that it ensures adequate bioavailability of the active substance, better than that of a conventional pharmaceutical preparation and largely independent of the gastric pH, it reduces fluctuations in the bioavailability of the active substance and it prevents malabsorption. Another advantageous property of the pharmaceutical composition according to the invention is the fact that it is suitable for all patients, i.e. including those in whom the gastric pH is increased by normal physiological variability, by disease or by co-medication with drugs which raise the gastric pH.

The dosage for oral use is expediently 25 to 300 mg of the active substance base (per capsule), preferably 50 to 200 mg, most preferably 75 to 150 mg of the active substance base, in each case once or twice a day.

The preferred ratio of acid to active substance is about 0.9:1 to about 4:1, most preferably between about 1:1 and 3:1. Preferably, at least one equivalent of acid is used per mol of the compound of formula I. The upper limit of about 4:1 (acid to active substance) is generally determined by the maximum acceptable size of the preparation in the desired dosages (number of pellets per capsule).

The Examples that follow are intended to illustrate the invention:

Example 1 a) Production of Core Material Containing Tartaric Acid Composition:

| gum arabic | 1 part by weight |
|---|---|
| tartaric acid | 20 parts by weight |

1 part by weight of gum arabic is dissolved In 4 parts by weight of purified water at 50° C. with stirring. Then 5 parts by weight of tartaric acid are dissolved in this solution with stirring.

8.3 parts by weight of tartaric acid crystals with an average particle size of 0.4 to 0.6 mm are placed in a suitable coating apparatus fitted with an air inlet and exhaust, and the pan is set in rotation. At an air inlet temperature of 60°-80° C. the tartaric acid crystals are sprayed at intervals with the solution of tartaric acid and gum arabic and sprinkled with a total of 6.7 parts by weight of powdered tartaric acid, so that roughly spherical particles are formed.

The spherical tartaric acid core material is then dried in the rotating pan at an air inlet temperature of 60°-80° C.

The core material is fractionated using a tumbler screening machine with perforated plates with a nominal mesh size of 0.6 and 0.8 mm. The product fraction between 0.6 and 0.8 mm is used in the rest of the process.

b) Insulation of the Core Material Containing Tartaric Acid Composition:

| core material containing tartaric acid | 23 parts by weight |
|---|---|
| gum arabic | 1 part by weight |
| talc | 2 parts by weight |

1 part by weight of gum arabic is dissolved in a mixture of 6.7 parts by weight of 96% ethanol and 13.5 parts by weight of purified water with stirring. Then 2 parts by weight of talc are dispersed in the solution with stirring.

In a fluidised bed processing apparatus, 23 parts by weight of core material containing tartaric acid are sprayed at an air inlet temperature of 35°-40° C. with the dispersion of gum arabic and talc by the under-bed spraying process.

The insulated core material containing tartaric acid is then dried in the circulating air drier at 40° C. for 8 hours.

To remove any lumps the dried insulated core material containing tartaric acid is screened through a screen with a nominal mesh size of 1.0 mm. The fraction of material with a particle size of <1 mm is further processed.

| | percentage composition | | | | per capsule [mg] | per capsule [mg] |
|---|---|---|---|---|---|---|
| | core material | insulating layer | active substance layer | total | | |
| tartaric acid | 61.3 | — | — | 61.3 | 176.7 | 353.4 |
| gum arabic | 3.1 | 2.8 | — | 5.9 | 17.0 | 34.0 |
| talc | — | 5.6 | 3.2 | 8.8 | 25.4 | 50.7 |
| hydroxypropylcellulose | — | — | 4.0 | 4.0 | 11.5 | 23.1 |
| active substance (mesylate of the compound of formula I) | — | — | 20.0 | 20.0 | 57.7* | 115.3** |
| total | | | | 100.0 | 288.3 | 576.5 |

*corresponds to 50 mg of the compound of formula 1 (active substance base)
**corresponds to 100 mg of the compound of formula 1 (active substance base)

c) Production of the Active Substance Layer
Composition:

| | |
|---|---|
| insulated core material containing tartaric acid | 91 parts by weight |
| hydroxypropylcellulose | 5 parts by weight |
| talc | 4 parts by weight |
| active substance (mesylate of BIBR 1048) | 25 parts by weight |

Hydroxypropylcellulose is dissolved in 168 parts by weight of 2-propanol with stirring and then the active substance and talc are dispersed in this solution with stirring.

In a fluidised bed processing apparatus, 91 parts by weight of insulated core material containing tartaric acid are sprayed at an air inlet temperature of 20°-30° C. with the dispersion containing the active substance by the under-bed spraying process.

The pellets containing the active substance are then dried in the circulating air drier at 35° C. for 8 hours.

To remove any lumps the pellets containing the active substance are screened through a screen with a nominal mesh size of 1.25 mm. The fraction of material with a particle size of <1.25 mm is further processed.

d) Packing Into Capsules

A quantity of active substance pellets containing in each case 50 or 100 mg of active substance base is packed into size 1 or size 0 elongated hard gelatine capsules or HPMC capsules by means of a capsule filling machine.

Example 2

The spherical tartaric acid core material is then dried in the rotating pan at an air inlet temperature of 60°-80° C.

The core material is fractionated using a tumbler screening machine with perforated plates with a nominal mesh size of 0.6 and 0.8 mm. The product fraction between 0.6 and 0.8 mm is used in the rest of the process.

b) Insulation of the Core Material Containing Tartaric Acid
Composition:

| | |
|---|---|
| core material containing tartaric acid | 23 parts by weight |
| gum arabic | 1 part by weight |
| talc | 2 parts by weight |

1 part by weight of gum arabic is dissolved in a mixture of 6.7 parts by weight of 96% ethanol and 13.5 parts by weight of purified water with stirring. Then 2 parts by weight of talc are dispersed in the solution with stirring.

In a fluidised bed processing apparatus, 23 parts by weight of core material containing tartaric acid are sprayed at an air inlet temperature of 35°-40° C. with the dispersion of gum arabic and talc by the under-bed spraying process.

The insulated core material containing tartaric acid is then dried in the circulating air drier at 40° C. for 8 hours.

To remove any lumps the dried insulated core material containing tartaric acid is screened through a screen with a nominal mesh size of 1.0 mm. The fraction of material with a particle size of <1 mm is further processed.

| | percentage composition | | | | | |
|---|---|---|---|---|---|---|
| | core material | insulating layer | active substance layer | total | per capsule [mg] | per capsule [mg] |
| tartaric acid | 38.5 | — | — | 38.5 | 55.5 | 166.5 |
| gum arabic | 1.9 | 1.7 | — | 3.6 | 5.2 | 15.6 |
| talc | — | 3.5 | 6.4 | 9.9 | 14.3 | 42.8 |
| hydroxypropylcellulose | — | — | 8.0 | 8.0 | 11.5 | 34.6 |
| active substance (mesylate of the compound of formula I) | — | — | 40.0 | 40.0 | 57.7* | 173.0** |
| total | | | | 100.0 | 144.2 | 432.5 |

*corresponds to 50 mg of the compound of formula 1 (active substance base)
**corresponds to 150 mg of the compound of formula 1 (active substance base)

a) Production of Core Material Containing Tartaric Acid
Composition:

| | |
|---|---|
| gum arabic | 1 part by weight |
| tartaric acid | 20 parts by weight |

1 part by weight of gum arabic is dissolved in 4 parts by weight of purified water at 50° C. with stirring. Then 5 parts by weight of tartaric acid are dissolved in this solution with stirring.

8.3 parts by weight of tartaric acid crystals with an average particle size of 0.4 to 0.6 mm are placed in a suitable coating apparatus fitted with an air inlet and exhaust, and the pan is set in rotation. At an air inlet temperature of 60°-80° C. the tartaric acid crystals are sprayed at intervals with the solution of tartaric acid and gum arabic and sprinkled with a total of 6.7 parts by weight of powdered tartaric acid, so that roughly spherical particles are formed.

c) Production of the Active Substance Layer
Composition:

| | |
|---|---|
| insulated core material containing tartaric acid | 57 parts by weight |
| hydroxypropylcellulose | 10 parts by weight |
| talc | 8 parts by weight |
| active substance (mesylate of BIBR 1048) | 50 parts by weight |

Hydroxypropylcellulose is dissolved in 335 parts by weight of 2-propanol with stirring and then the active substance and talc are dispersed in this solution with stirring.

In a fluidised bed processing apparatus, 91 parts by weight of insulated core material containing tartaric acid are sprayed at an air inlet temperature of 20°-30° C. with the dispersion containing the active substance by the under-bed spraying process.

The pellets containing the active substance are then dried in the circulating air drier at 35° C. for 8 hours.

To remove any lumps the pellets containing the active substance are screened through a screen with a nominal mesh size of 1.25 mm. The fraction of material with a particle size of <1.25 mm is further processed.

d) Packing Into Capsules

A quantity of active substance pellets containing in each case 50 or 150 mg of active substance base is packed into size 2 or size 0 hard gelatine capsules or HPMC capsules by means of a capsule filling machine.

Example 3

Preparation of ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate methanesulphonate

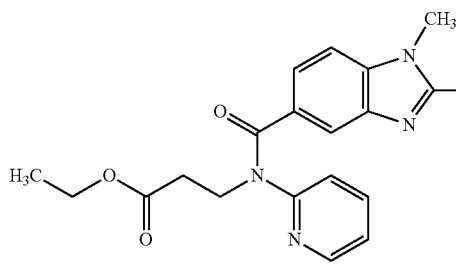 X 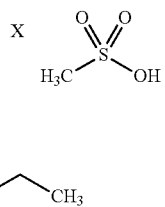

A solution of 5.0 mmol of methanesulphonic acid in 25 ml ethyl acetate was added dropwise, with stirring, to a solution of 3139 mg (5.0 mmol) of ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate base (prepared as described in WO 98/37075) in 250 ml ethyl acetate, at ambient temperature. After a few minutes the product began to crystallise out. It was stirred for another hour at ambient temperature and then for one more hour while cooling with ice, the precipitate was suction filtered, washed with about 50 ml of ethyl acetate and 50 ml of diethyl ether and dried at 50° C. in a circulating air drier.

Yield: 94% of theory
melting point: 178-179° C.
$C_{34}H_{41}N_7O_5 \times CH_4SO_3$ (723.86)

| Elemental analysis: | calc.: | C 58.07% | H 6.27% | N 13.55% | S 4.43% |
|---|---|---|---|---|---|
| | found: | 58.11% | 6.30% | 13.50% | 4.48% |

I claim:

1. A pharmaceutical composition for oral administration comprising:
   (a) a substantially spherical core material comprised of one or more pharmaceutically acceptable organic acids with a water solubility of >1 g / 250 mL at 20° C.; and
   (b) an active substance layer containing one or more binders and optionally a separating agent, wherein said active substance is ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate mesylate;
   (c) an insulating layer separating said core material and active substance layer, wherein said insulating layer is comprised of a water-soluble polymer, optionally with addition of suitable plasticizers, separating agents and pigments; and
   (d) an optional coating layer enclosing the active substance layer, wherein the pharmaceutical composition provides a patient with the active substance having a bioavailability that is therapeutically effective at normal and elevated gastric pH.

2. The pharmaceutical composition of claim 1, wherein the acceptable organic acid has a water solubility of > 1 g/160 mL at 25° C.

3. Pharmaceutical composition according to claim 1, wherein the pharmaceutically acceptable organic acid is selected from the group consisting of tartaric acid, fumaric acid, succinic acid, citric acid, malic acid, glutamic acid, aspartic acid and any combination thereof.

4. Pharmaceutical composition according to claim 1, wherein the pharmaceutically acceptable organic acid is selected from the group consisting of tartaric acid, fumaric acid, citric acid, succinic acid and any combination thereof.

5. Pharmaceutical composition according to claim 1, wherein the pharmaceutically acceptable organic acid is tartaric acid.

6. Pharmaceutical composition according to claim 1, wherein the content of ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate mesylate in the pharmaceutical composition is 5 to 60%.

7. Pharmaceutical composition according to claim 1, wherein the content of pharmaceutically acceptable organic acid is 20 to 90%.

8. Pharmaceutical composition according to claim 1, wherein said binder is selected from the group consisting of hydroxypropylcelluloses, hydroxypropylmethylcelluloses, methylcelluloses, hydroxyethylcelluloses, carboxymethylcelluloses, the polyvinylpyrrolidones, the copolymers of N-vinylpyrrolidone, vinyl acetate and any combination thereof.

9. Pharmaceutical composition according to claim 1, wherein said core material has an average particle size of 0.4 to 1.5 mm.

10. Pharmaceutical composition according to claim 1, wherein said water-soluble polymer is comprised of gum arabic or hydroxypropylmethylcellulose (HPMC).

11. Pharmaceutical composition according to claim 1, wherein said water-soluble polymer is comprised of a partially or totally synthetic polymer selected from the group consisting of hydroxypropylcelluloses, hydroxypropylmethylcelluloses, methylcelluloses, hydroxyethylcelluloses, carboxymethylcelluloses, the polyvinylpyrrolidones, the copolymers of N-vinylpyrrolidone, vinyl acetate, and any combination thereof.

12. Pharmaceutical composition according to claim 1, wherein the composition containing the active substance is packed into hard capsules.

13. Pharmaceutical composition of claim 12, wherein the hard capsule is hydroxypropylmethylcellulose (HPMC).

14. Pharmaceutical composition of claim 1, wherein the pharmaceutically acceptable organic acid is tartaric acid.

15. The pharmaceutical composition according to claim 1, wherein the core material consists of tartaric acid and gum arabic, the insulating layer consists of gum Arabic or hydroxypropylmethylcellulose and talc and the active substance layer consists of talc, hydroxypropylcellulose and ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate mesylate.

16. The pharmaceutical composition according to claim 15, wherein the tartaric acid in the core material is present in the composition at about 61.3%, the gum arabic in the core material is present in the composition at about 3.1%, the gum arabic in the insulating layer is present in the composition at about 2.8%, the talc in the insulating layer is present in the composition at about 5.6%, the talc in the active substance layer is present in the composition at about 3.2%, the hydroxypropylcellulose in the active substance layer is present in the composition at about 4.0% and the ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate mesylate in the active substance layer is present in the composition at about 20%.

17. The pharmaceutical composition according to claim 15, wherein the tartaric acid in the core material is present in the composition at about 38.5%, the gum arabic in the core material is present in the composition at about 1.9%, the gum arabic in the insulating layer is present in the composition at about 1.7%, the talc in the insulating layer is present in the composition at about 3.5%, the talc in the active substance layer is present in the composition at about 6.4%, the hydroxypropylcellulose in the active substance layer is present in the composition at about 8.0% and the ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate mesylate in the active substance layer is present in the composition at about 40%.

18. The pharmaceutical composition of claim 1, wherein the active substance layer contains from 50 mg to 200 mg of ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate.

19. The pharmaceutical composition of claim 1, wherein the active substance layer contains from 75 mg to 150 mg of ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate.

20. The pharmaceutical composition of claim 1, wherein the active substance layer contains 150 mg of ethyl 3-[(2-{[4-(hexyloxycarbonylamino-imino-methyl) -phenylamino]-methyl}-1-methyl-1H-benzimidazole-5-carbonyl)-pyridin-2-yl-amino]-propionate.

* * * * *